(12) United States Patent
Reynard

(10) Patent No.: US 6,428,501 B1
(45) Date of Patent: Aug. 6, 2002

(54) SURGICAL INSTRUMENT SLEEVE

(75) Inventor: Michael Reynard, Santa Monica, CA (US)

(73) Assignee: K2 Limited Partnership U/A/D, Santa Monica, CA (US)

(*) Notice: Subject to any disclaimer, the term of this patent is extended or adjusted under 35 U.S.C. 154(b) by 113 days.

(21) Appl. No.: 09/665,556

(22) Filed: Sep. 19, 2000

(51) Int. Cl.7 .............................. A61M 1/00; A61F 9/00
(52) U.S. Cl. .......................................... 604/27; 606/107
(58) Field of Search ............................. 604/22, 27, 28, 604/35, 44, 39, 43, 282; 606/107

(56) References Cited

U.S. PATENT DOCUMENTS

| | | | | |
|---|---|---|---|---|
| 5,741,226 A | * | 4/1998 | Strukel et al. ................. 604/35 |
| 5,743,871 A | * | 4/1998 | Strukel et al. ................. 604/35 |
| 6,048,348 A | * | 4/2000 | Chambers et al. ........... 606/107 |

* cited by examiner

Primary Examiner—Chen-Wen Jiang
(74) Attorney, Agent, or Firm—Albert O. Cota

(57) ABSTRACT

A surgical sleeve lens removal by laser or ultrasonic surgical instruments, also used on the forefront of an ophthalmic irrigation/aspiration surgical instrument. The surgical sleeve consists of a hollow sleeve body (20) with its proximal end (22) adapted to fit the surgical instrument and its distal end (24) having a tubular shank (30). The shank has a truncated cone contour (32) on its extremity and at least one annular protuberant appendage (34) integrally formed with the shank (30) and extending from an outside surface of the distal end, for manipulation of intraocular tissue. The appendage (34) has a sloped surface (36) and extends either partially or completely around the periphery of the sleeve body (20). The appendage (34) may consist of single or multiple elements but in any case the appendage has a larger outside diameter than the shank.

21 Claims, 3 Drawing Sheets

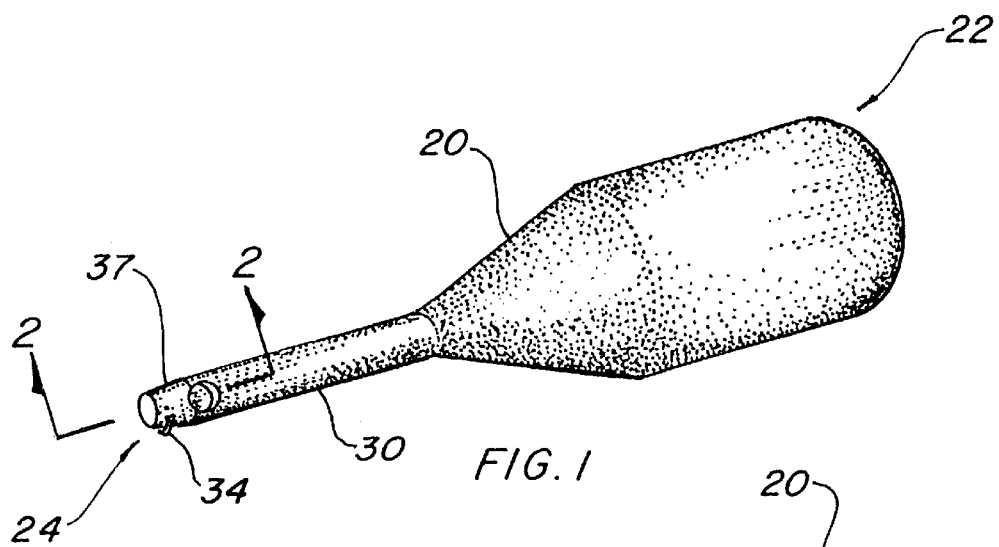
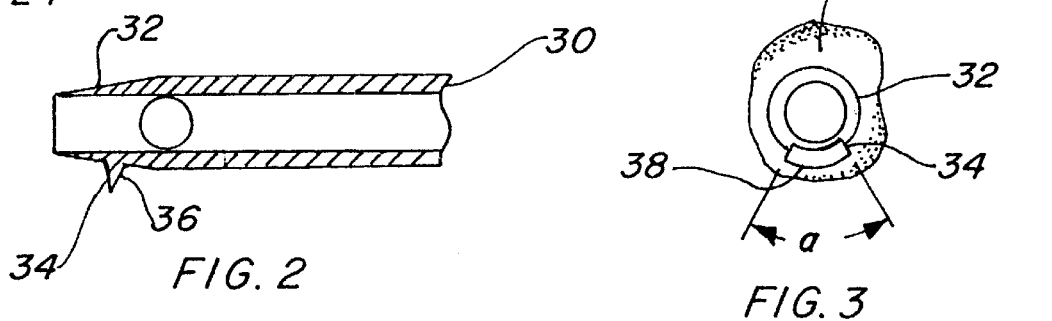

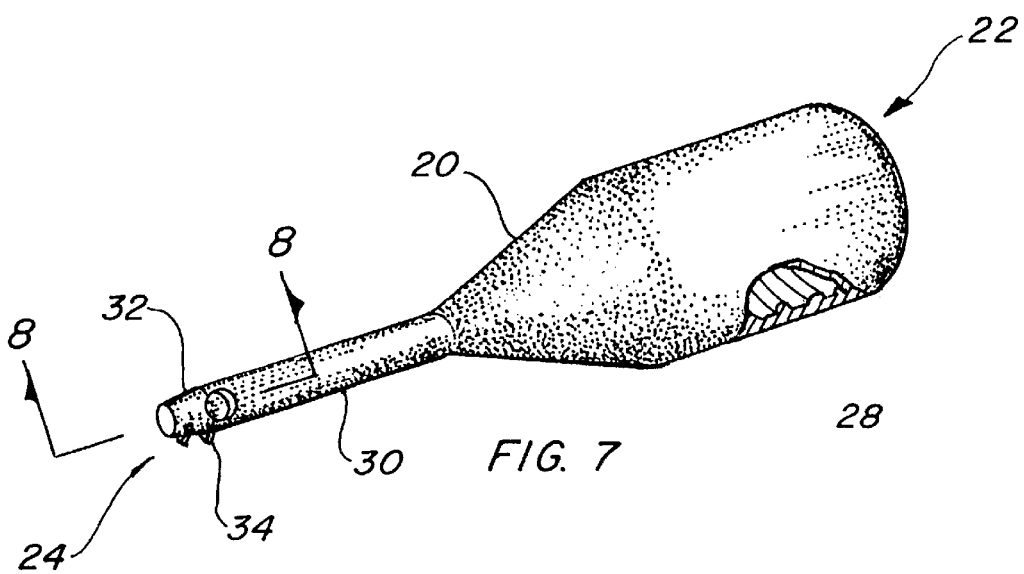
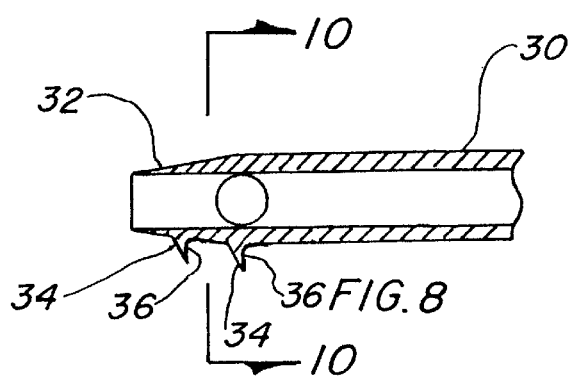
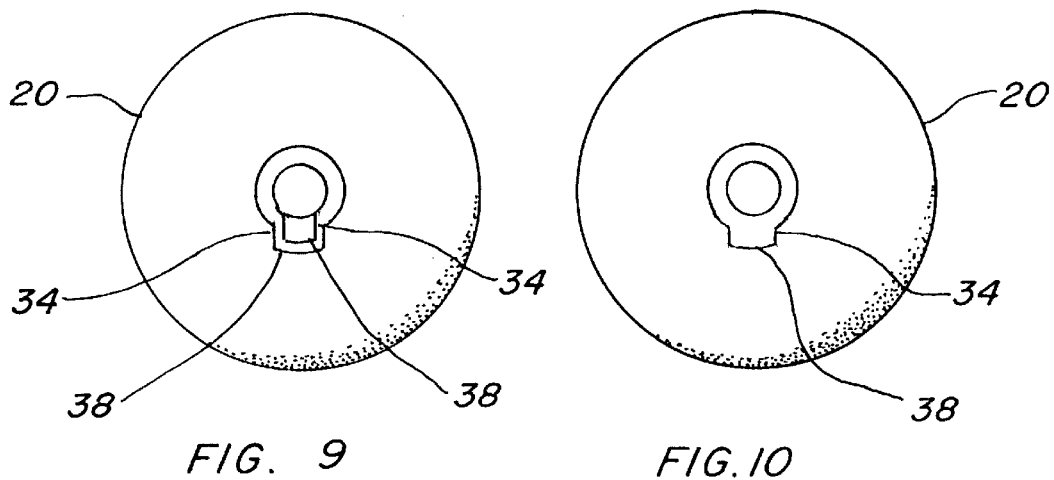

SURGICAL INSTRUMENT SLEEVE

TECHNICAL FIELD

The invention generally pertains to phacoemulsification instruments that are used to remove a cataract lens from a human eye, and, more particularly, to a resilient sleeve attached to the forefront of an ultrasonic surgical instrument.

BACKGROUND ART

Previously, many types of sleeves have been attached to a surgical instrument for ultrasonically removing the natural lens of a human eye. One type of surgical sleeve is positioned about the forefront of a phacoemulsification instrument and defines a conduit for the passage of fluid around the vibratory tip of the instrument. Many approaches have been taken for the configuration of this sleeve for various purposes, such as providing a clear passage for cooling fluid, conformance to a wound shape, automatic retraction, addition of guide ribs and conduit for light.

A search of the prior art did not disclose any patents that read directly on the claims of the instant invention, however the following U.S. patents are considered related:

| U.S. Pat. No. | Inventor | Issue Date |
| --- | --- | --- |
| 6,033,376 | Rockley | Mar. 7, 2000 |
| 5,984,904 | Steen et al. | Nov. 16, 1999 |
| 5,941,887 | Steen et al. | Aug. 24. 1999 |
| 5,807,310 | Hood | Sep. 15. 1998 |
| 5,478,338 | Reynard | Dec. 26, 1995 |
| 5,464,389 | Stahl | Nov. 7, 1995 |
| 5,354,265 | Mackool | Oct. 11, 1994 |
| 5,286,256 | Mackool | Feb. 15, 1994 |
| 5,282,786 | Ureche | Feb. 1, 1994 |
| 5,188,589 | Wypych et al. | Feb. 23, 1993 |
| 5,084,009 | Mackool | Jan. 28, 1992 |
| 4,983,160 | Steppe et al. | Jan. 8, 1991 |
| 4,897,079 | Zaleski et al. | Jan. 30, 1990 |
| 4,808,154 | Freeman | Feb. 28, 1989 |
| 4,652,255 | Martinez | Mar. 24, 1987 |

Rockley in U.S. Pat. No. 6,033,376 teaches a wound shaper sleeve having a wall configuration for controlling compression of the sleeve in order to cause the sleeve to shape and conform to the wound and limit fluid egress therefrom. A syringe attachment hub enables the syringe to be angularly displaced within the sleeve during phacoemulsification.

Steen et al in U.S. Pat. No. 5,984,904 discloses an array of spaced-apart protuberances on the interior wall surface to reduce the surface contact by defining a uniform network of fluid flow channels.

U.S. Pat. No. 5,941,887 issued to Steen, et al. is for a surgical sleeve having a series of spaced-apart rings on its interior wall for encircling the cutting tip. The sleeve encircles the tip in an unstressed condition and automatically retracts during use to expose the free end of the tip. The sleeve is able to remove heat from the tip eliminating the risk of burning the corneal tissue.

Hood in U.S. Pat. No. 5,807,310 teaches an irrigation sleeve having an outside band with a inner bore that extends the full length of the sleeve. The sleeve is constructed from silicone rubber and a band of a rigid material, such as TEFLON, which will not collapse in use.

Michael Reynard's own U.S. Pat. No. 5,478,338 is for a disposable sleeve in a tubular shape that has a plurality of fiber-optic bundles for transmission of light to enhance intraocular visualization during surgical use. Additional bundles of optical fibers may provide the application of laser beam and video transmission to the intraocular tissue.

Stahl in U.S. Pat. No. 5,464,389 teaches a sleeve and tip arrangement with the end of the working tip slotted and the sleeve having a first end portion that extends to the end of the tip and a second end portion terminating well before the tip end.

Mackool in U.S. Pat. No. 5,354,265 discloses two hollow infusion sleeves, with an outer sleeve conforming an incision and an inner sleeve preventing the outer sleeve from collapsing into a vibrating needle.

U.S. Pat. No. 5,286,256 issued to Mackool is for two hollow infusion sleeves with one conforming a surgical incision, thereby preventing leakage from the incision and the other preventing an outer sleeve from collapsing.

U.S. Pat. No. 5,282,786 issued to Ureche is for a sleeve having a flexible portion which permits retraction of the distal end, thus allowing contact between the tip of the tool and the body tissue removed. A rigid portion prevents collapse of the sleeve and permits fluid flow, thereby preventing overheating of the tip.

Wypych et al. in U.S. Pat. No. 5,188,589 teaches a sleeve having a rough texture of random bumps and pits on the interior surface of the tube for reducing the amount of surface contact between the cutting tip and the interior surface of the tube, thus assuring compression and bathing the cutting tip continuously in lubricant.

U.S. Pat. No. 5,084,009 issued to Mackool is for a hollow infusion sleeve conforming a surgical incision, thereby preventing leakage from the incision. A second embodiment has two sleeves with only the outer sleeve conforming to the incision.

Steppe et al. in U.S. Pat. No. 4,983,160 teaches a thin-walled tubular sleeve that extends from a hollow body to surround the aspiration conduit of the instrument. The body and sleeve are homogeneously molded from transparent thermoplastic which permits a rigid sleeve with a wall thickness of no more than 0.006 inches and a length-to-wall ratio of more that two.

U.S. Pat. No. 4,897,079 issued to Zaleski, et al. has a sleeve that includes a hollow sleeve portion with at least one fluid outlet at or near its distal end and a hub secured to the sleeve. The sleeve, which is disposable after use, is made of one or more organic polymeric materials and provides an effective fluid seal.

Freeman in U.S. Pat. No. 4,808,154 teaches a cylindrical sleeve member connected to the base of the tip having at least one internal longitudinally-extending rib to guide a flushing fluid through the cylindrical member and to isolate the interior wall portions of the sleeve from the tip.

U.S. Pat. No. 4,652,255 issued to Martinez discloses a flexible irrigating sleeve with a passage in the tip member with the irrigating sleeve providing an exit port in the distal end. A length of flexible aspirating tubing extends within the irrigating member and aspirates the material thorough the port in the distal end of the aspirating tip member.

For background purposes and as indicative of the art to which the invention is related, reference may be made to the following remaining patents found in the search:

| U.S. Pat. No. | Inventor | Issued |
|---|---|---|
| 3,896,811 | Storz | July 1975 |
| 4,014,333 | McIntyre | March 1977 |
| 4,417,578 | Banko | November 1983 |
| 4,531,934 | Kossovsky et al | July 1985 |
| 4,553,957 | Williams et al | November 1985 |
| 4,573,979 | Blake | March 1986 |
| 4,787,889 | Steppe et al | November 1989 |
| 4,816,017 | Hood | March 1989 |
| 4,816,018 | Parisi | March 1989 |
| 5,024,654 | Tyler | June 1991 |
| 5,151,084 | Khek | September 1992 |
| 5,199,943 | Wypych | April 1993 |
| 5,486,162 | Brumbach | January 1996 |
| 5,634,912 | Injev | February 1996 |
| 5,558,669 | Reynard | September 1996 |
| 5,591,160 | Reynard | January 1997 |
| 5,645,530 | Boukhny | July 1997 |
| 5,634,912 | Injev | June 1997 |
| 5,685,841 | Mackool | November 1997 |
| 5,741,226 | Strukel et al | April 1998 |
| 5,746,713 | Hood et al | May 1998 |
| 5,873,851 | Nilsson | February 1999 |
| 5,879,356 | Geuder | March 1999 |
| 5,957,928 | Kirwan | September 1999 |
| 5,989,209 | Barrett | November 1999 |
| 6,013,049 | Rockley | January 2000 |

DISCLOSURE OF THE INVENTION

The invention is an improvement of a surgical sleeve that is placed on the forefront of a phacoemulsification instrument or an irrigation/aspiration handpiece for ophthalmic surgery. The instrument consists of a handpiece containing a magneto-strictive mechanism which, using high frequency impulses, activates a hollow needle which is covered by the surgical sleeve. When the needle contacts an eye lens, a high-frequency vibration emulsifies the surrounding tissue and the displaced tissue particles are drawn under negative pressure into the hollow needle. Simultaneously, a saline solution is delivered between the sleeve and the outer wall of the needle for cooling and irrigation purposes.

A common problem in the state of the art removal of the lens tissue during cataract surgery in the presence of a constricted small pupil, is that the proximal tip of the vibrating needle is obscured behind the iris. Consequently, there is a higher risk of inadvertent rupture of lens zonules and lens capsule, which can result in vitreous prolapse into the anterior chamber and retinal problems, all of which are associated with visual impairment. Iris reactors for opening the pupil are cumbersome to operate and often result in pupillary sphincter tears and post-operative distortion of the pupil. Therefore, the primary object of the invention is to provide a surgical sleeve that has one or more annular protuberant appendages that serve to manipulate intraocular tissue during the surgical procedure. The medical practitioner may utilize the improved sleeve for retraction of the iris, thus achieving enhanced visualization of the entire surgical site.

An important object of the invention is the ability of the sleeve to sever or reposition intraocular scar tissue, including posterior synechiae, thereby enhancing the operating surgeons ability to perform intraocular procedures and lessen the possibility of surgical mishap. It is well known that adhesions between the iris and anterior lens capsule can inhibit pupillary dilation, thereby making cataract surgery more difficult. A second instrument is sometimes inserted through another surgical opening to severe these iris-lens adhesions, however, with the protuberance on the present invention the iris can be retracted and adhesions easily severed without the necessity of a separate tool.

Another object of the invention is that the improved surgical sleeve permits enhanced visualization of the haptics of an intraocular posterior chamber lens. At present, the surgeon is often unable to visually inspect and confirm positioning of posterior chamber lens baptics. Malpositioned haptics may result in decentration of a lens implant, which are often accompanied by visual aberrations including distortion or pronounced glare. It is not uncommon for patients who experience visual problems from decentered lenses to return to the operating room for necessary adjustments. Retraction of the iris at the time of surgery with the improved surgical sleeve permits direct inspection and manipulative adjustments of the lens implant.

Still another object of the invention is that the sleeve improvements are uncomplicated and inexpensive to produce, as only a simple tooling change is necessary and the injection molding procedure during manufacturing is minimally affected.

These and other objects and advantages of the present invention will become apparent from the subsequent detailed description of the preferred embodiment and the appended claims taken in conjunction with the accompanying drawings.

BRIEF DESCRIPTION OF THE DRAWINGS

FIG. 1 is a partial isometric view of the preferred embodiment.

FIG. 2 is a cross-sectional view taken along lines 2—2 of FIG. 1.

FIG. 3 is a partial front view of the preferred embodiment.

FIG. 4 is a partial isometric view of the second embodiment.

FIG. 5 is a cross-sectional view taken along lines 5—5 of FIG. 4.

FIG. 6 is a partial front view of the second embodiment.

FIG. 7 is a partial isometric view of the third embodiment.

FIG. 8 is a cross-sectional view taken along lines 8—8 of FIG. 7.

FIG. 9 is a partial front view of the third embodiment.

FIG. 10 is a cross-sectional view taken along the lines 10—10 of FIG. 8.

BEST MODE FOR CARRYING OUT THE INVENTION

Figure 11:
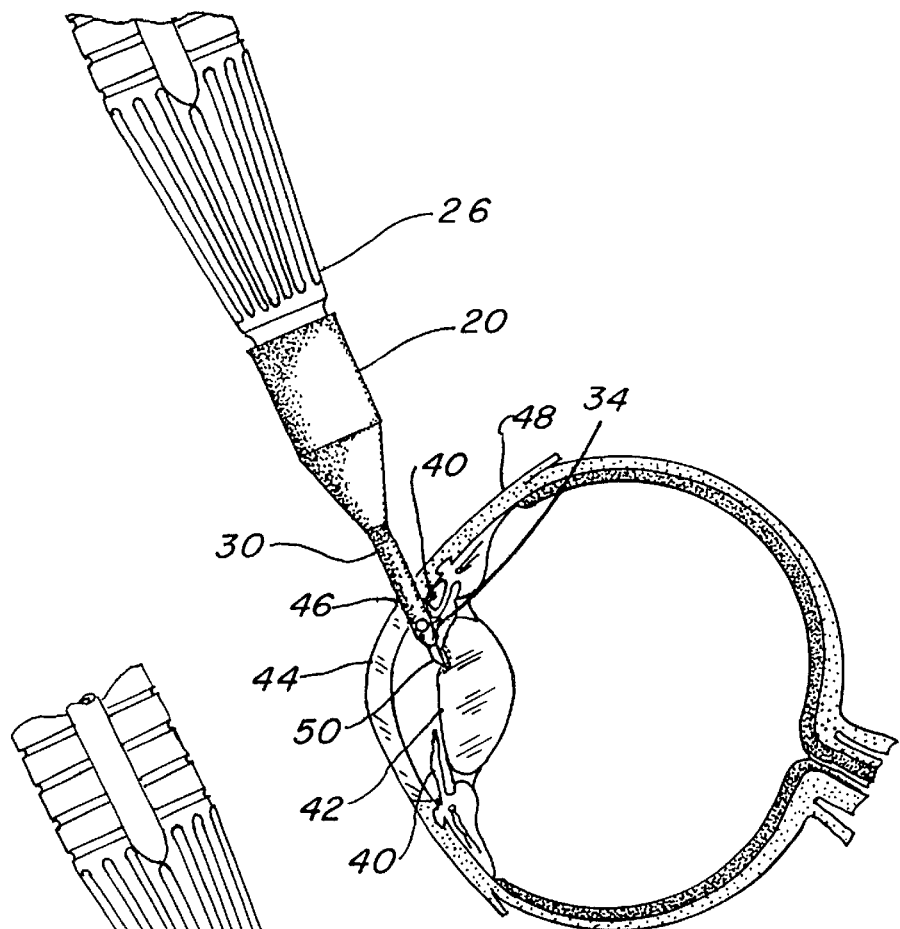
FIG. 11 is a cut-away diagram of a human eye with the sleeve in its preferred embodiment attached to the handpiece of a magneto-strictive ultrasonic surgical instrument with the sleeve and needle penetrating a incision through the cornea of an eye. The needle is emulsifying the lens and removing the liquefied particles through its hollow interior, and the annular protuberant appendage at the proximal tip of the sleeve is engaging the pupillary margin while retracting the iris.

The best mode for carrying out the invention is presented in terms of a preferred, second and third embodiment. All three embodiments are similar except for the number and extended configuration of the annular protuberant appendages. The preferred embodiment as shown in FIGS. 1 through 3 and 11, is comprised of a hollow sleeve body 20 that includes a proximal end 22 and a distal end 24.

The proximal end of the body 20 has a configuration that is adaptable to be removably attached to the forefront of a surgical instrument 26 for phacoemulsification and aspiration of a cataract lens of a human eye. A plurality of internal diametric ridges 28, as illustrated in FIG. 7, may be formed within the proximal end 22 for interfacing with, and gripping onto, the surgical instrument 26. However, these ridges are not requisite for the ultimate functioning of the invention and may equally well be formed as threads, on irregular surface, sockets or the like.

The distal end 24 of the body 20 is formed into a hollow tubular shank 30 with a truncated cone contour 32 on its extremity. The body 20 of the sleeve is preferably constructed of a thermoplastic material selected from a group consisting of hydroxymethylmethacrylate, polymide, polymethylmethacrylate, polyethylene, polyester, polystyrene, polypropylene, polytetrafluorethylene, polyurethane, and ethylene-vinyl-acetate or it may be constructed of silicone. Further the elastomeric material may have adhesive qualities, and in any case it should be pliable, resilient and non-absorbent.

At least one substantially annular protuberant appendage 34 is integrally formed with the shank 30 and extends from an outer surface of the distal end 24. The purpose of the protuberant appendage 34 is for manipulation of intraocular tissue as described previously. The annular protuberant appendage 34 has a sloped surface 36 relative to the tubular shank 30, which may be outwardly-sloped, as shown in FIG. 2, inwardly-sloped, as depicted in FIG. 5, or radially-sloped as illustrated in FIG. 8. The annular protuberant appendage 34 has a substantially circular shaped outer edge 38 that extends partially around the periphery of the sleeve body's distal end 24, preferably from 5 degrees to 45 degrees, as shown if FIGS. 3, 9 and 10, with FIG. 3 indicating the angular displacement with the alpha symbol "a". The annular protuberant appendage 34 is larger in its partial outside diameter than said distal end 24 of the tubular shank 30, and has a height above its adjoining surface from 0.003 inches (0.076 mm) to 0.015 inches (0.381 mm).

A second embodiment of the invention is illustrated in FIGS. 4 through 6, and has the annular protuberant appendage 34 with its circular shaped outer edge 38 extending completely around the periphery of the sleeve body's distal end 24. The annular protuberant appendage's sloped surface 36 may optionally be outwardly, inwardly or radially sloped.

A third embodiment of the invention is illustrated in FIGS. 7 through 10, and comprises a plurality of appendages 34 in parallel alignment with each other. The slope of the outer edge 38 is discretionary as is its height and shape.

In all of the embodiments the configuration of the annular protuberant appendage 34 is adaptable to engage and retract an ocular iris 40 and ocular lens tissue 42, as illustrated in FIG. 11. Similarly, the configuration permits engaging and severing abnormal intraocular scar tissue including adhesions and membranous deformities.

While the invention has been developed for use with a phacoemulsification surgical instrument 26, the surgical sleeve is readily adaptable to be attached to the forefront of any irrigation-aspiration handpiece of an instrument for ophthalmic surgery as well as a laser phacolysis surgical instrument.

Figure 12:
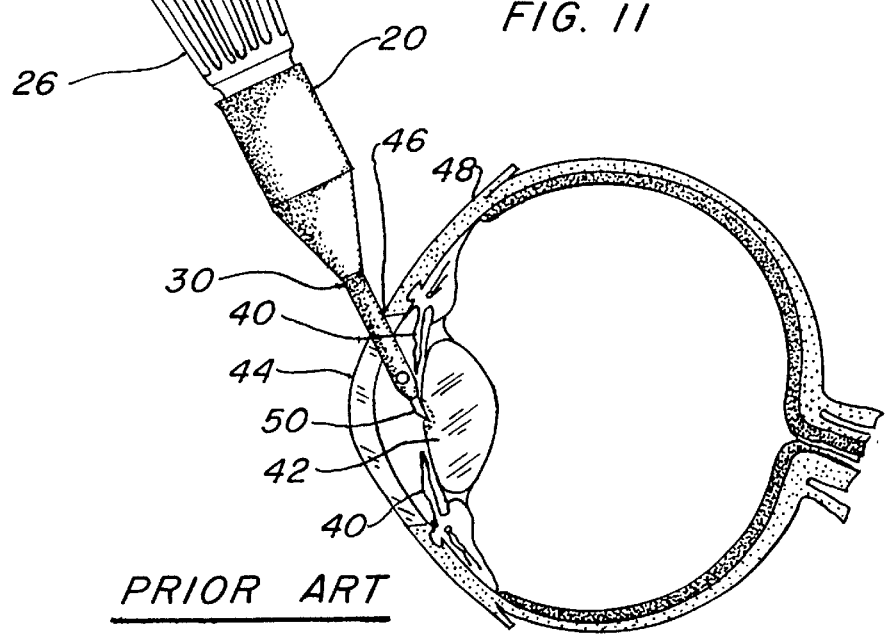
FIG. 12 represents prior art with a cut-away diagram of a human eye with a conventional sleeve attached to the handpiece of a magneto-strictive ultrasonic surgical instrument with the sleeve and needle penetrating an incision through the cornea of an eye while the needle is emulsifying the lens and removing liquefied particles through its hollow interior.

FIG. 12 illustrates the prior art with the surgical instrument 26 penetrating the cornea 44 through a surgical incision 46 with the needle of the instrument 26 engaging the ocular lens 42 and the area behind the iris 40 blocked from view. FIG. 11 depicts a human eye in cross section, with the iris 40 relocated by the annular protuberant appendage 34 to provide optimum visualization of the lens 42.

In use, the surgical sleeve covering the vibratory tip 50 of the phacoemulsification and aspiration surgical instrument 26 is inserted into a small surgical incision 46 through either the cornea 44, as illustrated, or through a constructed flap of a sclera 48. The vibratory tip 50 engages lens tissue 42 as the surgical sleeve delivers irrigating fluid for cooling the vibratory tip 50 and replacing intraocular volume. As a surgeon displaces the lens tissue 42, iris tissue 40 may interfere with visualization of the lens, particularly when the pupil of the iris 40 is constricted. It should be noted that pupillary constriction may result from intrastromal iris scarring, excessive pupillary sphincter action, posterior synechiae, topical and systemic medications and more commonly by an atrophied dilator muscle. Inadequate visualization increases the risk of inadvertent rupture of the lens zonules or lens capsule. In addition, surgical efficiency is reduced, thereby prolonging operating time and increasing the risk of corneal decomposition and post-surgical inflammation.

While the invention has been described in complete detail and pictorially shown in the accompanying drawings, it is not to be limited to such details, since many changes and modifications may be made to the invention without departing from the spirit and scope thereof Hence, it is described to cover any and all modifications and forms which may come within the language and scope of the appended claims.

What is claimed is:

1. A surgical sleeve for a phacoemulsification surgical instrument comprising:

a) a hollow sleeve body having a proximal end and a distal end, b) said proximal end having a configuration adaptable to be removably attached to said surgical instrument, c) said distal end having a tubular shank with a truncated cone contour on its extremity, and d) at least one substantially annular protuberant appendage integrally formed with said shank and extending from an outer surface of the distal end for manipulation of intraocular tissue.

2. The surgical sleeve for a phacoemulsification surgical instrument as recited in claim 1 wherein said hollow sleeve body is configured to be attached to the forefront of said surgical instrument.

3. The surgical sleeve for a phacoemulsification surgical instrument as recited in claim 1 wherein said sleeve is constructed of a thermoplastic material selected from a group consisting of hydroxymethylmethacrylate, polymide, polymethylmethacrylate, polyethylene, polyester, polystyrene, polypropylene, polytetrafluorethylene, polyurethane, and ethylene-vinyl-acetate.

4. The surgical sleeve for a phacoemulsification surgical instrument as recited in claim 1 wherein said sleeve is constructed of silicone.

5. The surgical sleeve for a phacoemulsification surgical instrument as recited in claim 1 wherein said sleeve is constructed of a material having adhesive qualities.

6. The surgical sleeve for a phacoemulsification surgical instrument as recited in claim 1 wherein said sleeve is constructed of a resilient non-absorbent material.

7. The surgical sleeve for a phacoemulsification surgical instrument as recited in claim 1 wherein said sleeve is constructed of a pliable elastomeric material.

8. The surgical sleeve for a phacoemulsification surgical instrument as recited in claim 1 further comprising a plurality of internal diametric ridges within the proximal end for interfacing with and gripping said surgical instrument.

9. The surgical sleeve for a phacoemulsification surgical instrument as recited in claim 1 wherein said annular protuberant appendage is formed integrally with the distal end of the truncated cone contour.

10. The surgical sleeve for a phacoemulsification surgical instrument as recited in claim 1 wherein said annular protuberant appendage further comprises a sloped surface relative to the tubular shank.

11. The surgical sleeve for a phacoemulsification surgical instrument as recited in claim 1 wherein said annular protuberant appendage further comprises a substantially circular shaped outer edge.

12. The surgical sleeve for a phacoemulsification surgical instrument as recited in claim 11 wherein said substantially circular shaped outer edge extends partially around the sleeve body distal end periphery.

13. The surgical sleeve for a phacoemulsification surgical instrument as recited in claim 12 wherein said substantially circular shaped outer edge extends from 5 degrees to 45 degrees around the sleeve body distal end periphery.

14. The surgical sleeve for a phacoemulsification surgical instrument as recited in claim 1 wherein said annular protuberant appendage's outer diameter is larger than said distal end tubular shank.

15. The surgical sleeve for a phacoemulsification surgical instrument as recited in claim 1 wherein said annular protuberant appendage has a height above its adjoining surface from 0.003 inches (0.076 mm) to 0.015 inches (0.381 mm).

16. The surgical sleeve for a phacoemulsification surgical instrument as recited in claim 1 wherein said annular protuberant appendage further comprises a plurality of appendages in parallel alignment.

17. The surgical sleeve for a phacoemulsification surgical instrument as recited in claim 1 wherein said annular protuberant appendage is adapted to engage and retract an ocular iris.

18. The surgical sleeve for a phacoemulsification surgical instrument as recited in claim 1 wherein said annular protuberant appendage is adapted to engage and severe abnormal intraocular scar tissue including adhesions and membranous deformities.

19. The surgical sleeve for a phacoemulsification surgical instrument as recited in claim 1 wherein said annular protuberant appendage is adapted to engage and manipulate ocular lens tissue.

20. A surgical sleeve adaptable to the forefront of an irrigation-aspiration handpiece of a instrument for ophthalmic surgery comprising:
   a) a hollow sleeve body having a proximal end and a distal end,
   b) said proximal end having a configuration adaptable to be removably attached to said handpiece,
   c) said distal end having a tubular shank with a truncated cone contour on its extremity, and
   d) at least one substantially annular protuberant appendage integrally formed with said shank and extending from an outer surface of the distal end for manipulation of intraocular tissue.

21. A surgical sleeve for a laser phacolysis surgical instrument comprising:
   a) a hollow sleeve body having a proximal end and a distal end,
   b) said proximal end having a configuration adaptable to be removably attached to said surgical instrument,
   c) said distal end having a tubular shank with a truncated cone contour on its extremity, and
   d) at least one substantially annular protuberant appendage integrally formed with said shank and extending from an outer surface of the distal end for manipulation of intraocular tissue.

* * * * *